United States Patent
Perego et al.

(10) Patent No.: US 6,872,859 B2
(45) Date of Patent: Mar. 29, 2005

(54) PROCESS FOR THE PREPARATION OF BISPHENOLS WITH ZEOLITES

(75) Inventors: Carlo Perego, Carnate-Milan (IT); Alberto De Angelis, Legnano-Milan (IT)

(73) Assignee: Enitecnologie S.p.A., San Donato Milanese (IT)

(*) Notice: Subject to any disclaimer, the term of this patent is extended or adjusted under 35 U.S.C. 154(b) by 0 days.

(21) Appl. No.: 10/478,865
(22) PCT Filed: May 28, 2002
(86) PCT No.: PCT/EP02/05845
§ 371 (c)(1), (2), (4) Date: Apr. 30, 2004
(87) PCT Pub. No.: WO02/096847
PCT Pub. Date: Dec. 5, 2002

(65) Prior Publication Data
US 2004/0171888 A1 Sep. 2, 2004

(30) Foreign Application Priority Data
May 30, 2001 (IT) .................................... MI2001A1143

(51) Int. Cl.$^7$ ............................................. C07C 39/16
(52) U.S. Cl. ....................... 568/728; 568/723; 568/727; 502/27; 502/29; 502/33
(58) Field of Search ................................ 568/727, 728, 568/723; 502/27, 29, 33

(56) References Cited

U.S. PATENT DOCUMENTS

| 3,496,239 | A |   | 2/1970 | Venuto et al. |
| 3,728,408 | A | * | 4/1973 | Tobias ......................... 568/822 |
| 4,306,106 | A | * | 12/1981 | Kerr et al. ..................... 585/640 |
| 4,777,301 | A | * | 10/1988 | Olson .......................... 568/727 |
| 4,795,847 | A |   | 1/1989 | Weitkamp et al. |
| 4,895,988 | A | * | 1/1990 | Clerici et al. ................ 568/727 |
| 6,207,866 | B1 | * | 3/2001 | Kawamata et al. ......... 568/723 |
| 6,492,566 | B1 | * | 12/2002 | Singh et al. ................ 568/727 |

FOREIGN PATENT DOCUMENTS

| EP | 1 068 898 | 1/2001 |
| WO | 93 10065 | 5/1993 |
| WO | 01 97969 | 12/2001 |

OTHER PUBLICATIONS

A.P. Singh: "Preparation of bisphenol–A over zeolite catalysts" Catalysis Letters, vol. 16, pp. 431–435 1992.
K. Nowinska et al.: "Synthesis of bisphenol–A over heteropoly compounds encapsulated into mesoporous molecular sieves" Applied Catalysis A: General, vol. 203, No. 1, pp. 91–100, Sep. 18, 2000.
D. Das et al.: "Sulfonic acid functionalized mesoporous MCM–41 silica as a convenient catalyst for Bisphenol–A synthesis" Chem. Commun., vol. 21, p. 2179 Oct. 5, 2001.

* cited by examiner

Primary Examiner—Michael L. Shipen
(74) Attorney, Agent, or Firm—Oblon, Spivak, McClelland, Maier & Neustadt, P.C.

(57) ABSTRACT

The present invention relates to a process for preparing bisphenols which comprises reacting a carbonyl compound containing at least two carbon atoms with an aromatic compound, containing a hydroxyl group and at least one hydrogen atom bound to the aromatic ring, in the presence of a catalyst comprising a zeolite characterized by a spaciousness index equal to or higher than 8. The invention also relates to a method for the regeneration of the zeolitic catalyst used in this process and comprises subjecting the exhausted catalyst to hot treatment with a suitable aromatic compound containing at least one activating group, preferably the same hydroxylated aromatic compound used in the process for the preparation of bisphenols from which the exhausted catalyst derives.

55 Claims, No Drawings

PROCESS FOR THE PREPARATION OF BISPHENOLS WITH ZEOLITES

The present invention relates to a process for preparing bisphenols which comprises reacting an aromatic compound containing a hydroxyl group with a carbonyl compound in the presence of a zeolite characterized by a spaciousness index equal to or higher than 8.

Bisphenols are products of great industrial interest and are mainly used for the synthesis of numerous polymeric materials and fine chemical products. They are products deriving from the condensation of two molecules of a phenolic compound with a molecule of a carbonyl compound. Among these, bisphenol A (4,4'-isopropylidenediphenol), is particularly important. This bisphenol, which is a condensation product between acetone and phenol, is the main derivative of phenol and has a rapidly expanding market (yearly increase of 7–10%). Bisphenol A is mainly used for the production of polycarbonates and epoxy resins and also for fine chemical products as flame retardants. Another bisphenol of industrial interest is bisphenol Z, the condensation product between phenol and cyclohexanone, which is used for the production of polycarbonate films.

Other bisphenols used are, for example:
1. o,o,o',o'-tetramethylbisphenol A which can be processed better than bisphenol A in that, as a polycarbonate, it has a much lower viscosity in the molten state and a greater resistance to hydrolysis;
2. 4,4' bis(hydroxyphenyl)-pentanoic acid, which is used for binding resins based on polyesters to phenolic resins;
3. Bisphenols A and Z containing an alkyl group in ortho which are used as drugs against coccidiosis in poultry.

These compounds are currently synthesized using mineral acids, especially hydrochloric acid, or sulfonic exchanger resins, as condensation catalysts. In the former case, mineral acids, in addition to creating possible problems of corrosion due to the presence of strong and concentrated acid, at the end of the reaction cycle must be separated from the product by neutralization with strong bases, obtaining the formation of considerable quantities of inorganic salts contaminated by aromatic products, which must be disposed of at the end of the process. Sulfonic resins overcome these problems relating to separation. Unfortunately however, their catalytic activity decreases with time due to the effect of fouling phenomena or the partial poisoning of the acid sites. When the residual activity is no longer such as to guarantee a correct running of the reaction, they must be substituted with fresh resin and the resin discharged can no longer be re-used and must be disposed of. The substitution of these two types of acids with solid and easily regenerable acids, such as zeolites, is therefore greatly desired both for environmental reasons and for the safety of the plant.

The patent EP 265017 describes the condensation of aromatics with carbonyl compounds such as, for example, the condensation of phenol with formaldehyde, carried out in the presence of zeolites belonging to the MFI group. A. P. Singh compares in "Catalysis Letters 16 (1992) 431–435, the activity of RE-Y, H—Y, H-mordenite, H-ZSM-5 zeolites with that of an ion exchange resin (Amberlyst-15) in the preparation of bisphenol A by the condensation of phenol with acetone.

The tests are carried out at 90° C. and at atmospheric pressure. The conversions of phenol with respect to RE-Y, H-mordenite, H—Y, H-ZSM-5, and Amberlyst-15 are respectively 4.61, 2.88, 0.51, 0.42 and 20.14%. The zeolites tested consequently have a much lower reactivity than that of sulfonic resins. The main reaction product is bisphenol A, followed by 2,4'-isopropylidenediphenol (ortho isomer). Chromanes, which are condensation by-products of the ortho isomer with a second acetone molecule, are formed in significant quantities, ranging from 4.6 to 15% by weight. These condensation products are harmful as they not only lower the reaction yield, but also contain only one free hydroxyl group. In the case of the synthesis of polycarbonates, these compounds consequently interrupt the polymeric chain growth, lowering the molecular weight of the polymer formed, thus causing a deterioration in quality.

The use of a zeolite, in particular beta zeolite, in the condensation of phenol with formaldehyde to give bisphenol F is described in JP 11269113: formaldehyde is an extremely reactive carbonyl compound and the condensation can be easily effected under rather bland reaction conditions.

The applicant has now found that zeolites characterized by a spaciousness index equal to or higher than 8, used under suitable reaction conditions, give higher performances than those described in the prior art and are also active in the condensation of phenolic compounds with carbonyl compounds having a much lower reactivity than that of formaldehyde.

The object of the present invention therefore relates to a process for preparing bisphenol compounds which comprises subjecting a carbonyl compound, containing at least two carbon atoms, to condensation with an aromatic compound containing a hydroxyl group and having at least one hydrogen atom bound to the aromatic ring, in the presence of a catalyst containing a zeolite having a spaciousness index greater than or equal to 8, at a temperature ranging from 120 to 250° C. and a pressure higher than the atmospheric value.

The spaciousness index is a parameter which provides a real measurement of the pore amplitude of materials such as zeolites and is described in "Zeolites and Related Microporous materials: state of art 1994", Studies in surface science and catalysis, vol. 84, (1994), page 37 onwards. The following table taken from U.S. Pat. No. 4,795,847, is also provided for illustrative purposes

| Zeolite | Spaciousness index |
| --- | --- |
| Y | 21 |
| ZSM-20 | 21 |
| Beta | 19 |
| L | 17 |
| MCM-22 = ERB-1 | 8 |
| Mordenite | 7 |
| NU-1 | 5 |
| Offretite | 5 |
| ZSM-12 | 3 |
| ZSM-5 | 1 |
| ZSM-22 | 1 |

Zeolites which can be well used in the process of the present invention are zeolites belonging to the BEA, FAU, MWW and LTL groups.

In particular, belonging to the BEA group is beta zeoite, described for the first time in U.S. Pat. No. 3,308,069, having the formula

wherein x is less than 1, preferably less than 0.75, Y varies from 5 to 100, W varies from 0 to 4, M is a metal of group IA, IIA and IIIA or a transition metal, n is the valence of M, Z is hydrogen, an ammonium ion or organic cation.

Modifications of beta zeolite obtained by partial or total isomorphous substitution of the aluminum of the zeolite with boron, iron or gallium, described in BE 877205 and EP 55046, also belong to the BEA group, together with beta zeolite containing controlled quantities of sodium, potassium, calcium or nickel described in EP 629599.

Zeolites of the FAU group preferably used are Y zeolite, described for the first time in U.S. Pat. No. 3,130,007 and ZSM-20 zeolite, described in U.S. Pat. No. 3,972,983, and a particularly preferred aspect is the use of Y zeolite.

Zeolites of the MWW group preferably used are MCM-22, described for the first time in U.S. Pat. No. 4,954,325 and ERB-1 described for the first time in EP 293,032.

The zeolite of the LTL group preferably used is L zeolite, described in U.S. Pat. No. 3,216,789.

The zeolites used in the process of the present invention are in acid form, i.e. in the form in which most of the cationic sites are occupied by hydrogen ions.

These zeolites can be used as such or bound with a ligand selected for example from alumina, silica, zirconia and magnesia.

A particularly preferred aspect of the present invention is to use beta zeolite, in acid form.

The beta zeolite can be advantageously used in the form bound with an inorganic ligand as described in EP 687500 and in EP 847802. In particular, the catalyst described in EP 687500, comprising a beta zeolite bound with an inorganic ligand, is characterized in that its extra-zeolitic porosity, i.e. the porosity obtained by summing up the mesoporosity and macroporosity of the catalytic composition itself, is such as to consist of a fraction of at least 25% of pores with a radius higher than 100 Å.

The catalyst described in EP 847802, comprising a beta zeolite bound with an inorganic ligand, having an extra-zeolitic porosity consisting of a fraction of at least 25% of pores with a radius higher than 100 Å, is characterized by a total volume of extra-zeolitic pores greater than or equal to 0.80 ml/g.

Aromatic compounds containing a hydroxyl group and having at least one hydrogen atom bound to the aromatic ring which can be conveniently used in the present invention are those represented by the following general formula:

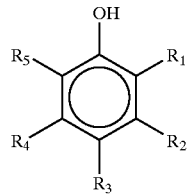

wherein the substituents $R_1$, $R_2$, $R_3$, $R_4$ and $R_5$, the same or different, are selected from H, linear alkyl containing from 1 to 6 carbon atoms and branched or cyclic alkyl containing from 3 to 6 carbon atoms, and wherein at least one of said substituents is hydrogen.

Phenol, cresol, xylenol are preferably used.

The carbonyl compound used is selected from aldehydes and ketones, and is preferably a compound having the general formula

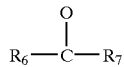

wherein $R_6$ is selected from linear alkyl containing from 1 to 6 carbon atoms, branched or cyclic alkyl containing from 3 to 6 carbon atoms, an aryl group and aryl substituted group;

and wherein $R_7$ is hydrogen and has the same meaning as $R_6$; or $R_6$ and $R_7$ together form a bivalent radical, containing 4 or 5 carbon atoms, ring closed on the carbonyl carbon atom.

A particularly preferred aspect of the present invention is to use acetaldehyde, benzaldehyde, acetone, methylethylketone, cyclohexanone and benzophenone, as carbonyl compounds.

According to a particularly preferred aspect of the present invention, two phenol molecules are condensed with an acetone molecule, in the presence of a zeolite having a spaciousness index greater than or equal to 8, preferably beta zeolite, to give bisphenol A. A preferred aspect of the present invention is also to prepare bisphenol Z (4,4' cyclohexylidenebisphenol) by condensing two phenol molecules with a molecule of cyclohexanone, in the presence of a zeolite having a spaciousness index greater than or equal to 8, preferably beta zeolite.

The process, object of the present-invention is preferably carried out at a temperature ranging from 130 to 230° C.

The condensation takes place in liquid phase, in a closed environment, at autogenous pressure. The pressure preferably ranges from 1.2 to 15 atmospheres.

It is also possible to operate in the presence of a solvent selected from toluene, xylene or trimethylbenzene.

The aromatic compound containing a hydroxyl group and the carbonyl compound are reacted in a molar ratio ranging from 2.2 to 15, preferably from 2.5 to 7.

The process can be carried out batchwise, in semi-continuous or in continuous: under semi-continuous conditions, in order to maintain a high aromatic compound/carbonyl compound ratio in the reactor containing the catalyst and the aromatic compound, the carbonyl compound is added gradually.

Under continuous conditions, the aromatic compound containing the hydroxyl group and the carbonyl compound are fed contemporaneously into the reactor containing the catalyst. The product and excess reagent (aromatic compound containing the hydroxyl group and at least one hydrogen atom bound to the aromatic ring) are then continuously discharged from the reactor.

In order to maintain a high aromatic compound/carbonyl compound ratio, the catalyst can be distributed into a reactor on several catalytic layers and the feeding of the carbonyl compound partialized at the beginning of each layer, whereas the feeding of the aromatic compound containing the hydroxyl group and at least one hydrogen atom bound to the aromatic ring is effected only at the beginning of the first layer.

The zeolites used in the process of the present invention, once exhausted or even only partially deactivated, can be regenerated by means of high temperature thermal treatment (500–600° C.) in an oxidative environment (oxygen or air). This in fact allows the combustion of the pitches present in the zeolite pores and regeneration of the material under such conditions as to allow it to be used again in the reaction.

We have now unexpectedly found a simpler and more economic method for regenerating these exhausted catalysts. The Applicant has in fact found that the zeolite-based catalysts used in the process of the present invention for the preparation of bisphenols by the reaction of an aromatic compound containing a hydroxyl group with a carbonyl compound, once deactivated by pitches, can be regenerated by means of hot treatment with a suitable aromatic compound.

This treatment not only removes the soluble component of the pitches, but is capable of also chemically degrading, by means of a reactive process, the insoluble pitches: the aromatic compound, in fact, reacts with the pitches, probable through a series of alkylation and/or transalkylation reactions catalyzed by the same zeolitic material, transforming the pitches into molecules characterized by a lower molecular weight soluble in the aromatic compound and, above all, capable of spreading through the zeolitic pores.

An object of the present invention therefore relates to a process for the regeneration of an at least partially exhausted zeolitic catalyst, coming from a process for preparing bisphenols by the condensation of a carbonyl compound containing at least two carbon atoms with an aromatic compound containing a hydroxyl group and having at least one hydrogen atom bound to the aromatic ring, in the presence of a catalyst comprising a zeolite having a spaciousness index greater than or equal to 8, at a temperature ranging from 120 to 250° C. and a pressure higher than the atmospheric value, said regeneration process comprising subjecting the exhausted catalyst to treatment with an aromatic compound containing at least one substituent selected from OH, O⁻, $NH_2$, NHR, $NR_2$, OR, NHCOR, in at least partially liquid phase and at a temperature equal to or higher than that at which the preparation process of bisphenols from which the exhausted catalyst derives, has been effected.

Aromatic compounds suitable for the treatment are aromatic compounds containing at least one activating group on the aromatic ring, preferably phenolic compounds, and even more preferably aromatic compounds having the general formula:

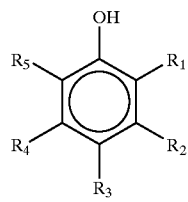

wherein the substituents $R_1$, $R_2$, $R_3$, $R_4$, and $R_5$, the same or different, are selected from H, linear alkyl containing from 1 to 6 carbon atoms and branched or cyclic alkyl containing from 3 to 6 carbon atoms, and wherein at least one of said substituents is hydrogen.

Phenol, cresol, xylenol are preferably used.

A preferred aspect of the present invention is for the aromatic compound used for the regenerating treatment to be the same as the aromatic compound containing a hydroxyl group of the process for the preparation of bisphenols from which the catalyst to be regenerated derives.

The temperature at which the regenerating treatment can be carried out ranges from 180° C. to 350° C., preferably from 250° C. to 350° C. The treatment is effected for a time ranging from 6 to 30 hours, preferably from 8 to 24 hours, and at a pressure ranging from 2 to 25 bars, preferably from 5 to 25 bars.

The regeneration process is preferably carried out at a temperature higher than that of the preparation process of bisphenols from which the exhausted catalyst derives.

The process of the present invention can be effected by recovering the exhausted catalyst from the bisphenol preparation reactor and subjecting it to regenerating treatment with the pre-selected aromatic compound in a specific reactor, but a preferred aspect of the present invention is for the regeneration process of the at least partially exhausted catalyst to be carried out in the bisphenol preparation reactor itself, by feeding the aromatic compound pre-selected for the regenerating treatment, after suspending the feeding of the reagents used for the synthesis of bisphenols. This embodiment is particularly convenient and preferred when the synthesis reactor of bisphenols is a continuous reactor, even more preferably a continuous reactor with a fixed catalytic bed.

When the regeneration process of the at least partially exhausted catalyst is carried out in the same bisphenol synthesis reactor, a particularly preferred aspect of the present invention is to use, as aromatic compound for the regenerating treatment, the hydroxylated aromatic substrate itself of the bisphenol synthesis process, after suspending the feeding of the carbonyl compound to the reactor. If the synthesis is carried out in the presence of a solvent, the feeding of the solvent to the reactor is also suspended.

This embodiment, in which the same hydroxylated aromatic substrate adopted in the synthesis process of bisphenols is used for the regeneration, is particularly convenient and preferred when the preparation reactor of bisphenols is a continuous reactor, even more preferably a continuous fixed catalytic bed reactor. In practice, according to this particular embodiment in continuous of the regeneration of the present invention, when the zeolitic catalyst used in the synthesis process of bisphenols of the present invention is exhausted, the feeding stream of the carbonyl compound to the alkylation reactor is suspended, whereas the stream of aromatic substrate containing the hydroxyl group continues to be fed to the reactor, optionally by raising the temperature of the catalytic bed when the regeneration treatment is to be effected at a higher temperature than that of the synthesis process of bisphenols. A preferred aspect is that the stream of aromatic substrate containing the hydroxyl group be fed to the reactor in countercurrent.

When the regeneration process has terminated, the feeding of the carbonyl compound is re-started to re-initiate the synthesis process of bisphenols, after possible cooling of the catalytic bed.

According to a preferred aspect of the present invention, an exhausted catalyst based on beta zeolite coming from a synthesis process of bisphenol A by the reaction of phenol with acetone, is regenerated in the synthesis reactor of bisphenol A itself, using the stream of phenol.

In all these cases in which the regeneration is effected in the synthesis reactor of bisphenols itself, and said reactor is in continuous, the operating WHSV preferably ranges from 0.1 to 20 hours⁻¹, even more preferably from 1 to 10 hours¹.

In accordance with what is specified above, a further aspect of the present invention relates to a process for preparing bisphenols which comprises the following steps:
a) condensation of a carbonyl compound containing at least two carbon atoms with an aromatic compound containing a hydroxyl group and having at least one hydrogen atom bound to the aromatic ring, in the presence of a catalyst comprising a zeolite having a spaciousness index greater than or equal to 8, at a temperature ranging from 120 to 250° C. and at a pressure higher than the atmospheric value, until said catalyst shows at least partial deactivation;
b) suspension of the feeding of the carbonyl compound and treatment of said deactivated catalyst with the sole feeding of the aromatic substrate containing the hydroxyl group, in at least partially liquid phase and at a temperature at least equal to and preferably higher than the temperature of the condensation process of step a) until the at least partial regeneration of the catalyst,
c) reactivation of the feeding of the carbonyl compound, after re-establishing the temperature conditions used in the condensation in step a) as the regeneration is preferably carried out at a temperature higher than that of the condensation step.

The multi-step process described above is preferably used for the preparation of bisphenol A by the reaction of phenol and acetone in the presence of a catalytic composition containing beta zeolite, which is regenerated in the same synthesis reactor of bisphenol A using the stream of phenol.

EXAMPLE 1

Synthesis of Beta Zeolite 58.8 g of tetraethylammonium hydroxide at 40% by weight in aqueous solution and 1.9 g of sodium aluminate (56% of $Al_2O_3$) are added to 58.4 g of demineralized water. The mixture is heated to about 80° C. and is left under stirring until complete dissolution.

The limpid solution thus obtained is added to 37.5 g of LUDOX HS colloidal silica at 40% by weight of $SiO_2$. A homogeneous suspension is obtained, having a pH equal to 14, which is charged into a steel autoclave and left to crystallize under hydro-thermal conditions at 150° C. for 10 days, under static conditions and autogenous pressure.

The crystallized product is separated by filtration, re-dispersed in demineralized water and re-filtered. A humid panel of zeolite is obtained, containing the organic templating agent tetraethylammonium and sodium.

The humid zeolitic panel, prepared as described above, is dried in an oven for 1 hour at 150° C., calcined in muffle for 5 hours at 550° C. in a stream of air.

The calcined solid is dispersed in an aqueous solution of ammonium acetate for ion exchange. This zeolite in ammonium form is calcined in muffle for 5 hours at 550° C. in a stream of air obtaining beta zeolite in acid form.

Upon elemental chemical analysis, the sodium residue of this zeolite is 106 ppm whereas the aluminum content is equal to 3.14% ([Al]/[Na]=252).

The product is characterized by means of X-ray diffraction from powders.

EXAMPLE 2

Synthesis of ERB-1 Zeolite

An alkaline solution consisting of sodium hydroxide is charged into a 1000 cm³ three-necked flask equipped with a reflux cooler and rod stirrer. The solution is brought to the desired temperature (70–80° C.) by means of a heating jacket and the aluminum source, consisting of sodium aluminate, is then added, under stirring, obtaining a limpid solution. The organic templating agent consisting of hexamethyleneimine is added to the reaction mixture and the silica source, consisting of Areosil 200, is then slowly added.

| Molar ratios | $SiO_2/Al_2O_3$ | $N/SiO_2$ | $Na^+/SiO^2$ | $OH^-/SiO_2$ | $H_2O/SiO_2$ |
|---|---|---|---|---|---|
| | 30 | 0.35 | 0.18 | 0.18 | 45 |

At the end of the addition, the reaction mixture is kept under magnetic stirring for about four hours at the temperature indicated above and is then cooled to room temperature and left in static aging for 24 hours. A homogeneous slurry is obtained, which is charged into a stainless steel autoclave, placed in a rocking oven and kept under stirring for 10 days at a temperature of 150° C.

At the end of the reaction, a suspension is discharged, from which a solid is recovered by filtration, which, after repeated washings with demineralized water, is dried in an oven at 120° C. The dried solid is characterized by means of X-ray diffraction from powders (XRD). The solid is then calcined at 550° C. for 5 hours in a stream of air.

A material is obtained, which has the same diffraction spectrum indicated in FIG. 4 and table 3 of European patent 293,032.

This material is then exchanged with ammonium acetate and obtained in acid form.

EXAMPLE 3

Synthesis of ZSM-12 Zeolite 2.4 g of sodium aluminate at 56% of $Al_2O_3$ are dissolved in 84 g of an aqueous solution of tetraethylammonium hydroxide at 35%. The limpid solution thus obtained is poured, under stirring, into 200 g of Ludox HS40 colloidal silica. After brief stirring, a limpid, homogeneous gel is obtained, which is poured into an AISI316 stainless steel autoclave, equipped with an anchor stirrer. The gel is crystallized under hydro-thermal conditions at 165° C. for 90 hours. At this point, the autoclave is cooled and the solid separated from the mother liquor and washed with demineralized water until the washing water has a pH of less than 9.

The solid is calcined in an atmosphere of air for 5 hours. The material is then exchanged with ammonium acetate and obtained in acid form.

The solid is then definitely separated from the aqueous environment, dried and calcined for 5 hours at 500° C. in an atmosphere of air. The zeolitic catalyst is thus obtained in acid form. An XRD analysis is carried out on the final sample, which reveals the presence of the MTW crystalline phase alone, and also a chemical analysis on the basis of which the residual sodium proves to be less than 50 ppm and the molar ratio $SiO_2/Al_2O_3$ is 102.

EXAMPLE 4

Synthesis of Bisphenol A with Beta Zeolite—Batch Test 9.4 g of phenol (0.1 moles) and 1.16 g (0.02 moles) of acetone, molar ratio phenol/acetone=5/1, and 1 g of Beta zeolite prepared according to Example 1, with a molar ratio $SiO_2/Al_2O_3$=25, a spaciousness index of 19, previously treated at 550° C. in a stream of air to obtain the acid form starting from the ammonium form, are charged into a glass autoclave. The autoclave is closed and is kept under stirring for 12 hours at 180° C.

At the end, the mass is cooled to room temperature. The reaction product is analyzed by means of mass G.C. with the analytical method described in Analytical Chemistry, volume 40, number 14, December 1968, pages 2212–2215.

Acetone conversion: 99.9%
Selectivity to p,p' Bisphenol A: 48.97%
Selectivity to o,p' Bisphenol A: 27.3%
Selectivity to trimers and heavy products: 23.73%
Selectivity to mesityl oxide (undesired by-product): lower than the analytical limit (0.01%)
Selectivity to chromanes (undesired by products): lower than the analytical limit (0.01%)

EXAMPLE 5

Synthesis of Bisphenol A with Y Zeolite—Batch Test 9.4 g of phenol (0.1 moles) and 1.16 g (0.02 moles) of acetone, molar ratio phenol/acetone=5/1, and 1 g of Y zeolite, Toyosoda HSH-320 HUA with a molar ratio $SiO_2/Al_2O_3=5.5$, a spaciousness index of 21, previously treated at 550° C. in a stream of air, are charged into a glass autoclave. The autoclave is closed and is kept under stirring for 12 hours at 180° C.

At the end, the mass is cooled to room temperature. The reaction product is analyzed by means of mass G.C. with the analytical method described in Analytical Chemistry, volume 40, number 14, December 1968, pages 2212–2215.
Acetone conversion: 90.94%
Selectivity to p,p' Bisphenol A: 38.42%
Selectivity to o,p' Bisphenol A: 21.46%
Selectivity to trimers and heavy products: 40.11%
Selectivity to mesityl oxide (undesired by-product): lower than the analytical limit (0.01%)
Selectivity to chromanes (undesired by products): lower than the analytical limit (0.01%)

EXAMPLE 6

Synthesis of Bisphenol A with ERB-1 Zeolite—Batch Test 9.4 g of phenol (0.1 moles) and 1.16 g (0.02 moles) of acetone, molar ratio phenol/acetone=5/1, and 1 g of ERB-1 zeolite, iso-structural with MCM-22 zeolite, with a molar ratio $SiO_2/Al_2O_3=30$, a spaciousness index of 8, prepared according to the procedure described in Example 2 and previously treated at 550° C. in a stream of air, are charged into a glass autoclave. The autoclave is closed and is kept under stirring for 12 hours at 180° C.

At the end, the mass is cooled to room temperature. The reaction product is analyzed by means of mass G.C. with the analytical method described in Analytical Chemistry, volume 40, number 14, December 1968, pages 2212–2215.
Acetone conversion: 81.5%
Selectivity to p,p' Bisphenol A: 44.2%
Selectivity to o,p' Bisphenol A: 21.27%
Selectivity to trimers and heavy products: 47.27%
Selectivity to mesityl oxide (undesired by-product) lower than the analytical limit (0.01%)
Selectivity to chromanes (undesired by products): lower than the analytical limit (0.01%)

EXAMPLE 7 COMPARATIVE

Synthesis of Bisphenol A with ZSM-12 Zeolite—Batch Test 9.4 g of phenol (0.1 moles) and 1.16 g (0.02 moles) of acetone, molar ratio phenol/acetone=5/1, and 1 g of ZSM-12 zeolite, with a molar ratio $SiO_2/Al_2O_3=102$, a spaciousness index of 3, prepared according to the procedure described in Example 2 and previously treated at 550° C. in a stream of air, are charged into a glass autoclave. The autoclave is closed and is kept under stirring for 12 hours at 180° C.

At the end, the mass is cooled to room temperature. The reaction product is analyzed by means of mass G.C. with the analytical method described in Analytical Chemistry, volume 40, number 14, December 1968, pages 2212–2215.
Acetone conversion: 76.43%
Selectivity to p,p' Bisphenol A: 11.43%
Selectivity to o,p' Bisphenol A: 7.9%
Selectivity to trimers and heavy products: 34.45%
Selectivity to mesityl oxide (undesired by-product): 46.22%

EXAMPLE 8

Synthesis of Bisphenol Z with Beta Zeolite—Batch Test 9.4 g of phenol (0.1 moles) and 3.27 g (0.033 moles) of cyclohexanone, molar ratio phenol/cyclohexanone=3/1, and 1 g of Beta zeolite, prepared according to Example 1, with a molar ratio $SiO_2/Al_2O_3=25$, a spaciousness index of 19, previously treated at 550° C. in a stream of air, are charged into a glass autoclave. The autoclave is closed and is kept under stirring for 6 hours at 160° C.

At the end, the mass is cooled to room temperature. The reaction product is analyzed by means of mass G.C. with the analytical method described in Analytical Chemistry, volume 40, number 14, December 1968, pages 2212–2215.
Cyclohexanone conversion: 100%
Selectivity to p,p' Bisphenol Z: 31.53%
Selectivity to o,p' Bisphenol Z: 68.47%
Selectivity to trimers and heavy products: 0%

EXAMPLE 9

Synthesis of Bisphenol A with Beta Zeolite—Test in Continuous 5 cm³ of beta zeolite prepared according to Example 1, previously treated at 550° C. in a stream of air to obtain the acid form starting from the ammonium form and sieved at 70–100 mesh, are charged into a tubular reactor having a diameter of 12.5 mm and a length of 390 mm. A mixture of phenol/acetone are then fed to the reactor in a molar ratio of 10/1, at a temperature of 180° C., at a pressure of four bars and an LHSV of 2 h$^{-1}$.

The reaction product is analyzed by means of mass G.C. with the analytical method described in Analytical Chemistry, volume 40, number 14, December 1968, pages 2212–2215.
Acetone conversion: 99.87%
Selectivity to p,p' Bisphenol A: 52.9%
Selectivity to o,p' Bisphenol A: 32.5%
the complement to 100% consisting of condensation products with a higher molecular weight.

EXAMPLE 10

Regeneration Test

The previous example is repeated and prolonged until the acetone conversion drops to 92% with a selectivity to bisphenol A (p,p' isomer+o,p' isomer) in. the reaction product of 78%, the complement to 100 consisting of condensation products with a higher molecular weight.

At this point the regeneration procedure of the partially exhausted catalyst is activated:
  the feeding of the phenol-acetone mixture is interrupted, whereas pure phenol is fed at the same space velocity;
  the catalytic bed is heated to a temperature of 280° C. by subjecting the reactor to a counterpressure of eleven bars;
  the temperature reached is maintained for 8 hours, feeding pure phenol for this period at the same space velocity;
  the catalytic bed is brought back to the reaction temperature (180° C.).

At the end of the reaction procedure described, the feeding of the phenol-acetone mixture 10/1 is re-started, obtaining an acetone conversion of 99.96% with a selectivity to bisphenol A (p,p' isomer+o,p' isomer) in the reaction product of 85.37%, the complement to 100 consisting of condensation products with a higher molecular weight.

EXAMPLE 11

Regeneration Test

The previous example is repeated and prolonged until the conversion of the acetone fed drops to 91.8%.

At this point the regeneration procedure of the partially exhausted catalyst is activated. The feeding of the phenol-acetone mixture is interrupted, whereas pure phenol is fed at the same space velocity;

the catalytic bed is heated to a temperature of 250° C. by subjecting the reactor to a counterpressure of eleven bars;

the temperature reached is maintained for 8 hours, feeding pure phenol for this period at the same space velocity;

the catalytic bed is brought back to the reaction temperature (180° C.).

At the end of the reaction procedure described, the feeding of the phenol-acetone mixture 10/1 is re-started, obtaining an acetone conversion of 98.48% with a selectivity to bisphenol A (p,p' isomer+o,p' isomer) in the reaction product of 85.51%, the complement to 100 consisting of condensation products with a higher molecular weight.

EXAMPLE 12

Comparative Regeneration Test 5 cm³ of beta zeolite, previously treated at 550° C. in a stream of air to obtain the acid form starting from the ammonium form and sieved at 70–100 mesh, are charged into a tubular reactor having a diameter of 12.5 mm and a length of 390 mm. A mixture of phenol/acetone are then fed to the reactor in a molar ratio of 10/1, at a temperature of 180° C., at a pressure of four bars and an LHSV of 2 h⁻¹.

An acetone conversion of 99.87% is obtained, with a selectivity to bisphenol A (p,p' isomer+o,p' isomer) in the reaction product of 85.42%, the complement to 100 consisting of condensation products with a higher molecular weight.

The test is prolonged until the acetone conversion drops to 92% with a selectivity to bisphenol A (4,4' BFA+2,2 BFA) in the reaction product of 78%, the complement to 100 consisting of condensation products with a higher molecular weight.

At this point the regeneration procedure of the partially exhausted catalyst is activated:

the feeding of the phenol-acetone mixture is interrupted, whereas n-decane is fed at the same space velocity;

the catalytic bed is heated to a temperature of 280° C. by subjecting the reactor to a counterpressure of 11 bars;

the temperature reached is maintained for 8 hours, feeding pure phenol for this period at the same space velocity;

the catalytic bed is brought back to the reaction temperature (180° C.).

At the end of the reaction procedure described, the feeding of the phenol-acetone mixture 10/1 is re-started, obtaining an acetone conversion of 91% with a selectivity to bisphenol A (p,p' isomer+o,p' isomer) in the reaction product of 76%, the complement to 100 consisting of condensation products with a higher molecular weight.

It can therefore be noted how the washing with n-decane, contrary to what occurs for the phenol, is not capable of re-establishing either the conversion or the initial selectivity.

What is claimed is:

1. A process for preparing bisphenol compounds which comprises
subjecting to condensation a carbonyl compound containing at least two carbon atoms with an aromatic compound, containing a hydroxyl group and having at least one hydrogen atom bound to the aromatic ring, in the presence of a catalyst comprising at least one zeolite belonging to a group selected from the group consisting of BEA, MWW and LTL, at a temperature ranging from 120 to 250° C. and a pressure higher than atmospheric pressure.

2. The process according to claim 1, wherein the process is carried out in the presence of a zeolite belonging to the BEA group and the zeolite is beta zeolite, which may be modified by partial or total isomorphous substitution of the aluminum of the zeolite with boron, iron or gallium, or the zeolite is a beta zeolite comprising of sodium, potassium, calcium or nickel.

3. The process according to claim 1, wherein the process is carried out in the presence of zeolite of the MWW group and the zeolite is at least one of a MCM-22 or a ERB-1 zeolite.

4. The process according to claim 1, wherein the process is carried out in the presence of a zeolite of the LTL group and the zeolite is L zeolite.

5. The process according to claim 1, wherein the zeolite is in acid form.

6. The process according to claim 1, wherein the zeolite is bound with at least one binder selected from the group consisting of alumina, silica, zirconia and magnesia.

7. The process according to claim 1, wherein the process is carried out in the presence of a beta zeolite in acid form.

8. The process according to claim 1, wherein the catalyst comprises a beta zeolite bound with an inorganic binder and has an extra-zeolitic porosity of at least 25% of pores with a radius higher than 100 Å.

9. The process according to claim 1, wherein the catalyst comprises a beta zeolite bound with an inorganic binder and has an extra-zeolitic porosity of at least 25% of pores with a radius higher than 100 Å, and has a total extra-zeolitic pore volume greater than or equal to 0.80 ml/g.

10. The process according to claim 1, wherein the aromatic compound containing a hydroxyl group and having at least one hydrogen atom bound to the aromatic ring is represented by the following formula:

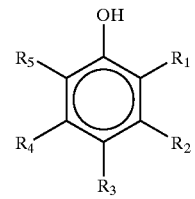

wherein the substituents $R_1$, $R_2$, $R_3$, $R_4$ and $R_5$, may be the same or different, and are selected from the around consisting of H, linear alkyl containing from 1 to 6 carbon atoms, branched alkyl containing from 3 to 6 carbon atoms, and a cyclic alkyl containing from 3 to 6 carbon atoms, and wherein at least one of said substituents is hydrogen.

11. The process according to claim 10, wherein the aromatic compound is at least one selected from the group consisting of phenol, cresol and xylenol.

12. The process according to claim 1, wherein the carbonyl compound, is at least one of an aldehyde or a ketone, and has the formula:

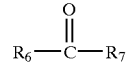

wherein $R_6$ is selected from the group consisting of a linear alkyl containing from 1 to 6 carbon atoms a branched alkyl containing from 3 to 6 carbon atoms, a cyclic alkyl containing from 3 to 6 carbon atoms, an aryl group and an aryl substituted group;

and wherein $R_7$ is hydrogen or has the same meaning as $R_6$; or wherein $R_6$ and $R_7$ together form a bivalent radical, containing 4 or 5 carbon atoms, ring closed on the carbonyl carbon atom.

13. The process according to claim 12, wherein the carbonyl compound is selected from the group consisting of acetaldehyde, acetone, benzaldehyde, methyl ethylketone, cyclohexanone and benzophenone.

14. The process according to claim 1 wherein two phenol molecules are condensed with an acetone molecule, in the presence of a catalyst comprising a zeolite belonging to a group selected from the group consisting of BEA, MWW and LTL having a spaciousness index greater than or equal to 8.

15. The process according to claim 14, wherein the zeolite is beta zeolite.

16. The process according to claim 1 wherein two phenol molecules are condensed with an cyclohexanone molecule, in the presence of a catalyst comprising a zeolite belonging to a group selected from the group consisting of BEA, MWW and LTL having a spaciousness index greater than or equal to 8.

17. The process according to claim 16, wherein the zeolite is beta zeolite.

18. The process according to claim 15, wherein the beta zeolite may be modified by partial or total isomorphous substitution of the aluminum of the zeolite with boron, iron or gallium, or is a beta zeolite comprising at least one of sodium, potassium, calcium or nickel.

19. The process according to claim 15, wherein the zeolite is in acid form.

20. The process according to claim 15, wherein the zeolite is bound with a binder selected from the group consisting of alumina, silica, zirconia and magnesia.

21. The process according to claim 15, wherein the catalyst comprises a beta zeolite bound with an inorganic binder and has an extra-zeolitic porosity of at least 25% of pores with a radius higher than 100 Å.

22. The process according to claim 15, wherein the catalyst comprises a beta zeolite bound with an inorganic binder, has an extra-zeolitic porosity of at least 25% of pores with a radius higher than 100 Å, and has a total extra-zeolitic pore volume greater than or equal to 0.80 ml/g.

23. The process according to claim 1, carried out at a temperature ranging from 130 to 230° C.

24. The process according to claim 1, wherein the pressure is from 1.2 to 15 atmospheres.

25. The process according to claim 1, wherein the aromatic compound containing a hydroxyl group and the carbonyl compound are present in a molar ratio of from 2.2 to 15.

26. The process according to claim 25, wherein the molar ratio is from 2.5 to 7.

27. The process according to claim 1, carried out in the presence of at least one solvent selected from the group consisting of toluene, xylene and trimethylbenzene.

28. The process according to claim 1, carried out batchwise, semi-continuously or continuously.

29. The process according to claim 28, carried out continuously, wherein the catalyst is distributed in a reactor on several catalytic layers and the carbonyl compound is at least partialized fed at the beginning of each layer, and the aromatic compound containing the hydroxyl group and at least one hydrogen atom bound to the aromatic ring is fed only at the beginning of the first layer.

30. A process for the regeneration of an at least partially exhausted zeolitic catalyst, obtained from a process for the preparation of bisphenol compounds which includes condensing a carbonyl compound containing at least two carbon atoms with an aromatic compound containing a hydroxyl group and having at least one hydrogen atom bound to the aromatic ring, in the presence of a catalyst comprising a zeolite having a spaciousness index higher than or equal to 8, at a temperature ranging from 120 to 250° C. and a pressure higher than atmospheric pressure, said regeneration process comprising:

subjecting the at least partially exhausted zeolitic catalyst to treatment with an aromatic hydrocarbon containing at least one substituent selected from the group consisting of at least OH, O$^-$, NH$_2$, NHR, NR$_2$ OR, and NHCOR, in at least a partially liquid phase and at a temperature equal to the temperature at which the process for the preparation bisphenol compounds from which the exhausted catalyst derives, is carried out.

31. The process according to claim 30, wherein the aromatic hydrocarbon is a phenolic compound.

32. The process according to claim 31, wherein the phenolic compound has the formula:

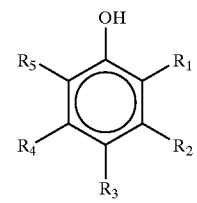

wherein the substituents $R_1$, $R_2$, $R_3$, $R_4$, and $R_5$, may be the same or different, and are H, a linear alkyl containing from 1 to 6 carbon atoms, a branched alkyl containing from 3 to 6 carbon atoms or a, cyclic alkyl containing from 3 to 6 carbon atoms, and wherein at least one of $R_1$, $R_2$, $R_3$, $R_4$ or $R_5$ is hydrogen.

33. The process according to claim 32, wherein the aromatic hydrocarbon is the same as the aromatic compound containing a hydroxyl group present in the process for the preparation of bisphenols from which the exhausted catalyst derives.

34. The process according to claim 30, carried out at a temperature of from 180° C. to 250° C., at a pressure of from 2 to 25 bars and for a time of from 6 to 30 hours.

35. The process according to claim 34, carried out at a temperature of from 250° C. to 350° C., at a pressure of from 5 to 25 bars and for a time of from 8 to 24 hours.

36. The process according to claim 30, wherein the zeolitic catalyst is a catalyst comprising at least one zeolite of the BEA, FAU, MWW or LTL groups.

37. The process according to claim 36, wherein the zeolite is beta zeolite.

38. The process according to claim 30, carried out in the same reactor wherein the preparation of bisphenol is carried out.

39. The process according to claim 38, wherein the reactor is a continuous reactor.

40. The process according to claim 39, wherein the reactor is a continuous fixed bed reactor.

41. The process according to claim 33, wherein the treatment is carried out continuously and wherein the aromatic hydrocarbon is the same aromatic substrate containing a hydroxyl group present in the process for the preparation of bisphenols.

42. The process according to claim 41, wherein an exhausted catalyst comprising a beta zeolite obtained from a synthesis process of bisphenol A by the reaction of phenol with acetone, is regenerated in the same synthesis reactor with a stream of phenol.

43. A process according to claim 1, further comprising when the catalyst:
   a) is at least partially deactivated;
   a) treating said at least partially deactivated catalyst with the aromatic substrate, in at least a partially liquid phase and at a temperature at least equal to the temperature of the condensation process of a) until the catalyst is at least partially regenerated,
   b) adding the carbonyl compound to the at least partially regenerated catalyst, after optionally re-establishing the temperature conditions used in the condensation in a) if the regeneration has been carried out at a temperature higher than that of the condensation step.

44. The process according to claim 43, wherein the regeneration is carried out at a WHSV of from 1 to 20 hours$^{-1}$.

45. The process according to claim 44, wherein the regeneration is carried out at a WHSV of from 2 to 8 hours$^{-1}$.

46. The regeneration process according to claim 30, wherein the temperature at which the regeneration of the exhausted catalyst is carried out is higher than the temperature of the process for the preparation of bisphenols from which the exhausted catalyst is obtained.

47. The process according to claim 41, wherein the regeneration treatment is carried out by feeding the aromatic substrate containing a hydroxyl group in countercurrent.

48. The process according to claim 29, wherein the carbonyl compound is acetone, the aromatic compound containing the hydroxyl group is phenol and the feeding of acetone to the synthesis reactor of bisphenols is carried out in a partialized way.

49. The process according to claim 17, wherein the beta zeolite may be modified by partial or total isomorphous substitution of the aluminum of the zeolite with boron, iron or gallium, or a beta zeolite comprises at least one of sodium, potassium, calcium or nickel.

50. The process according to claim 17, wherein the zeolite is in acid form.

51. The process according to claim 17, wherein the zeolite is bound with at least one binder selected from the group consisting of alumina, silica, zirconia and magnesia.

52. The process according to claim 17, wherein the catalyst comprises a beta zeolite bound with an inorganic binder and has an extra-zeolitic porosity of at least 25% of pores with a radius higher than 100 Å.

53. The process according to claim 17, wherein the catalyst comprises a beta zeolite bound with an inorganic binder, has an extra-zeolitic porosity of at least 25% of pores with a radius higher than 100 Å, and has a total extra-zeolitic pore volume greater than or equal to 0.80 ml/g.

54. The process according to claim 40, wherein the regeneration treatment is carried out continuously and wherein the aromatic hydrocarbon is the same aromatic substrate containing a hydroxyl group present in the process for the preparation of bisphenols.

55. The process according to claim 54, wherein the carbonyl compound is acetone, the aromatic compound containing the hydroxyl group is phenol and the feeding of acetone to the synthesis reactor of bisphenols is carried out in a partialized manner.

* * * * *